(12) United States Patent
Schroering

(10) Patent No.: US 8,651,863 B2
(45) Date of Patent: Feb. 18, 2014

(54) BAND OF CONNECTIVE TISSUE GROOVES FOR USE WITH A DENTAL IMPLANT OR A SEPARATE ABUTMENT FOR A DENTAL IMPLANT

(76) Inventor: Robert Schroering, Louisville, KY (US)

( * ) Notice: Subject to any disclaimer, the term of this patent is extended or adjusted under 35 U.S.C. 154(b) by 55 days.

(21) Appl. No.: 13/093,630

(22) Filed: Apr. 25, 2011

(65) Prior Publication Data

US 2011/0200969 A1 Aug. 18, 2011

Related U.S. Application Data

(63) Continuation-in-part of application No. 12/048,417, filed on Mar. 14, 2008, now abandoned, which is a continuation-in-part of application No. 11/420,379, filed on May 25, 2006, now abandoned, which is a continuation-in-part of application No. 10/404,700, filed on Apr. 1, 2003, now Pat. No. 7,097,453.

(51) Int. Cl.
*A61C 13/12* (2006.01)
*A61C 8/00* (2006.01)

(52) U.S. Cl.
USPC .......................................... 433/172; 433/173

(58) Field of Classification Search
USPC ............... 433/172–176, 201.1; 606/301–330; 623/17.11, 17.17–17.18, 23.74
See application file for complete search history.

(56) References Cited

U.S. PATENT DOCUMENTS

| | | |
|---|---|---|
| 4,206,516 A | 6/1980 | Pilliar |
| 4,547,327 A | 10/1985 | Bruins et al. |
| 4,713,003 A | 12/1987 | Symington et al. |
| 4,713,004 A | 12/1987 | Linkow et al. |
| 4,723,913 A | 2/1988 | Bergman |
| 4,960,381 A | 10/1990 | Niznick |
| 5,022,860 A | 6/1991 | Lazzara et al. |
| 5,049,074 A | 9/1991 | Otani et al. |
| 5,052,929 A | 10/1991 | Seal |
| 5,108,289 A | 4/1992 | Fukuyo |
| 5,236,458 A | 8/1993 | Ducheyne |
| 5,269,685 A | 12/1993 | Jorneus |
| 5,344,457 A | 9/1994 | Pilliar et al. |
| 5,370,692 A | 12/1994 | Fink et al. |
| 5,427,527 A | 6/1995 | Niznick et al. |
| 5,433,606 A | 7/1995 | Niznick et al. |
| 5,478,237 A | 12/1995 | Ishizawa |
| 5,484,286 A | 1/1996 | Hansson |
| 5,527,183 A | 6/1996 | O'Brien |
| 5,571,017 A | 11/1996 | Niznick |
| 5,588,838 A * | 12/1996 | Hansson et al. ............... 433/173 |
| 5,591,029 A * | 1/1997 | Zuest ............................ 433/173 |
| 5,601,429 A | 2/1997 | Blacklock |
| 5,603,338 A | 2/1997 | Beaty |

(Continued)

OTHER PUBLICATIONS

Adell, R. et al, A 15-year study of osseointegrated implants in the treatment of the edentulous jaw, Int. J. Oral Surg., 1981, pp. 387-416, v. 10, Munksgaard, Copenhagen, Denmark.

*Primary Examiner* — Yogesh Patel

(74) *Attorney, Agent, or Firm* — Joan L. Simunic

(57) ABSTRACT

The present invention is a dental implant system that has a band of connective tissue rings and grooves on an external surface of the dental implant system. The connective tissue band grooves have a depth of from greater than about 25 μm to about 600 μm. The dental implant system is designed to minimize tissue loss and to reduce the risk of bacterial infection in the implant site.

9 Claims, 10 Drawing Sheets

(56) References Cited

U.S. PATENT DOCUMENTS

| | | |
|---|---|---|
| 5,685,715 A | 11/1997 | Beaty et al. |
| 5,695,336 A | 12/1997 | Lazzara |
| 5,709,547 A | 1/1998 | Lazzara et al. |
| 5,727,943 A | 3/1998 | Beaty et al. |
| 5,755,574 A | 5/1998 | D'Alise |
| 5,759,035 A | 6/1998 | Ricci |
| 5,766,009 A | 6/1998 | Jeffcoat |
| 5,863,201 A | 1/1999 | Lazzara et al. |
| 5,885,079 A | 3/1999 | Niznick |
| 5,915,967 A | 6/1999 | Clokie |
| 5,926,685 A | 7/1999 | Krebs et al. |
| 5,989,027 A | 11/1999 | Wagner et al. |
| 6,036,491 A | 3/2000 | Hansson |
| 6,095,817 A | 8/2000 | Wagner et al. |
| 6,102,703 A | 8/2000 | Day |
| 6,379,153 B1* | 4/2002 | Schroering .............. 433/173 |
| 6,419,491 B1 | 7/2002 | Ricci et al. |
| 6,454,569 B1 | 9/2002 | Hollander et al. |
| 6,527,554 B2 | 3/2003 | Hurson et al. |
| 6,547,564 B1* | 4/2003 | Hansson ................ 433/174 |
| 6,981,873 B2* | 1/2006 | Choi et al. ............. 433/173 |
| 7,097,453 B1* | 8/2006 | Schroering, Jr. ........ 433/173 |
| 2003/0120279 A1* | 6/2003 | Hansson ................. 606/73 |
| 2004/0006346 A1* | 1/2004 | Holmen et al. ........... 606/73 |
| 2006/0263748 A1 | 11/2006 | Schroering |
| 2007/0298379 A1 | 12/2007 | D'Alise |
| 2009/0233256 A1 | 9/2009 | Schroering |
| 2010/0112520 A1* | 5/2010 | Worthington ........... 433/169 |

* cited by examiner

BAND OF CONNECTIVE TISSUE GROOVES FOR USE WITH A DENTAL IMPLANT OR A SEPARATE ABUTMENT FOR A DENTAL IMPLANT

CROSS-REFERENCE TO PRIOR APPLICATIONS

The present application is a continuation-in-part application of U.S. patent application Ser. No. 12/048,417 filed Mar. 14, 2008, now abandoned, which is a continuation-in-part application of U.S. patent application Ser. No. 11/420,379 filed May 25, 2006, now abandoned, which is a continuation-in-part application of U.S. patent application Ser. No. 10/404,700 filed Apr. 1, 2003, now U.S. Pat. No. 7,097,453, all of which are incorporated herein by reference.

BACKGROUND

The present invention is a dental implant system having a unique band of connective tissue rings and grooves. The band may be part of a dental implant or part of a separate abutment that is used in conjunction with a dental implant. The band is designed to minimize tissue loss and to reduce the risk of bacterial infection in the implant site. The band is intended to be positioned on the portion of the implant or the abutment such that when the dental implant system is mounted within a patient's jawbone, the connective tissue band is positioned within the connective tissue layer, or soft tissue, adjacent to the bone.

Dental implants are embedded in the jaw bone and serve to anchor one or more artificial teeth or dentures. Typically, the implant is set in the bone and an abutment is mounted on the implant. Important to the success of such devices is the rigid anchoring of the implant in the bone, and several journal articles and patents have proposed various methods for achieving rigid anchoring (see U.S. Pat. No. 5,344,457 and incorporated herein by reference). For example, U.S. Pat. No. 4,713,003, issued to Symington et al. describes an implant that has a tapered external body, resulting in a better distribution of the stresses acting on the device in situ than is achieved with cylindrical body implants. U.S. Pat. No. 5,344,457, issued to Pilliar et al, describes an implant that has a body with a non-porous surface on the upper portion of the implant and a porous surface on the lower portion of the implant. The porous surface provides interstices into which bone is permitted to grow once the implant is accommodated within the bone.

As reported in U.S. Pat. No. 6,454,469, issued to Hollander et al, and incorporated herein by reference, it is known to provide a variety of surface effects to enhance osseo-stability of the implant within bone. In the '469 patent a device is taught that has a collar portion consisting of proximal and distal cylindrical sub-segments, one having a surface effect adapted for the promotion of growth of soft tissue and the other adapted for the promotion of bone or hard tissue growth. Specifically, the '469 patent teaches a dental implant having a distal segment with a surface that defines an ordered micro-geometric repetitive surface pattern in the form of a multiplicity of alternating ridges and grooves, each having a fixed or established width in a range of about 2.0 to about 25 microns and a fixed or established depth in the range of about 2.0 to about 25 microns. While the device of the '469 patent recognizes that bone and soft tissue react differently with implant surfaces, it fails to recognize that academic studies have demonstrated that pore sizes of 10 microns or less lead to little or no fibrous ingrowth, and that a pore size of greater than about 30 microns is needed to give sufficient blood supply for adequate blood vessel ingrowth. This ingrowth is believed to be a factor in impeding epithelial migration toward the boney region of the implant site, and the less epithelial migration into the site, the lower the probability of infection development.

As is known in the art, the abutment of the dental implant generally has a first portion that abuts the implant and that is preferably positioned so as to lie within the connective tissue layer, a second portion that abuts the first portion and is preferably positioned so as to lie within the attached epithelial layer, and a third portion that abuts the second portion and is preferably positioned so as to lie within the sulcular epithelial layer. Each of the tissue layers are generally believed to be about 1 mm in depth.

Because of its proximity to the bone, it is imperative that the connective tissue forms a tight bond with the first portion of the abutment. If gaps remain between the connective tissue and the abutment, bacteria may penetrate into the gap and into the boney region, causing infection. The prior art has recognized the need for the connective tissue segment of the abutment to have a surface designed to encourage tissue attachment to the abutment. For example, U.S. Pat. No. 6,527,554, issued to Hurson, et al., teaches a dental implant system that has a soft tissue attachment zone. To promote attachment of connective soft tissues, the soft tissue attachment zone is preferably roughened, and is at least about twice as rough as the smooth machined and/or polished surfaces of prior art abutments in the transgingival region. U.S. Pat. No. 6,419,491, issued to Ricci, et al., teaches a dental implant with a platform section that has a first ordered microgeometric repetitive surface pattern at a distal section and a second ordered geometric pattern at a proximal portion. The second ordered geometric pattern, which exhibits a width of about 2 to about 25 microns and a depth in a range of about 2 to about 25 microns, is deemed to be more suitable for purpose of tissue (as opposed to bone) adhesion or interface. U.S. Pat. No. 6,981,873, issued to Choi, et al., teaches a dental implant with a settling portion formed between an abutment portion and a fixture portion, wherein the average surface textures of the settling portion is between about 1.0 µm to about 2.0 µm.

Although progress has been made with respect to addressing the adhesion of connective tissue to dental implants, the implants of the prior art still fail to promote the degree of adhesion needed to reduce the risk of bacterial infection.

SUMMARY OF THE PREFERRED EMBODIMENT

The present invention is a dental implant system having a band of connective tissue rings and grooves. This connective tissue band may be part of a dental implant or part of a separate abutment that is used in conjunction with a dental implant. The connective tissue band is on an external surface of a stem of the dental implant system. It is intended that the connective tissue band be positioned on the dental implant system such that when the dental implant system is mounted within a patient's jawbone, the connective tissue band is positioned within the connective tissue layer adjacent to the bone.

The connective tissue band comprises a plurality of a repetitive pattern of rings and grooves wherein the rings define a ring width of from greater than about 25 µm to about 600 µm, and more preferably from about 30 µm to about 450 µm, and the grooves define a groove width of from greater than about 25 µm to about 600 µm, and more preferably from about 30 µm to about 150 µm. The rings and grooves further define a groove depth of from greater than about 25 µm to about 600 μm, and more preferably from about 30 μm to about 400 μm. To minimize the risk that contamination can transverse into the implant site, each groove is isolated from its neighboring grooves by the closed-loop rings. The dental implant may further comprise bone locking grooves having a depth approximately twice the depth of the connective tissue grooves thereby allowing the implant to be "locked" into the bone with resultant stabilization of the implant.

DETAILED DESCRIPTION OF THE PREFERRED EMBODIMENT

Figure 1:
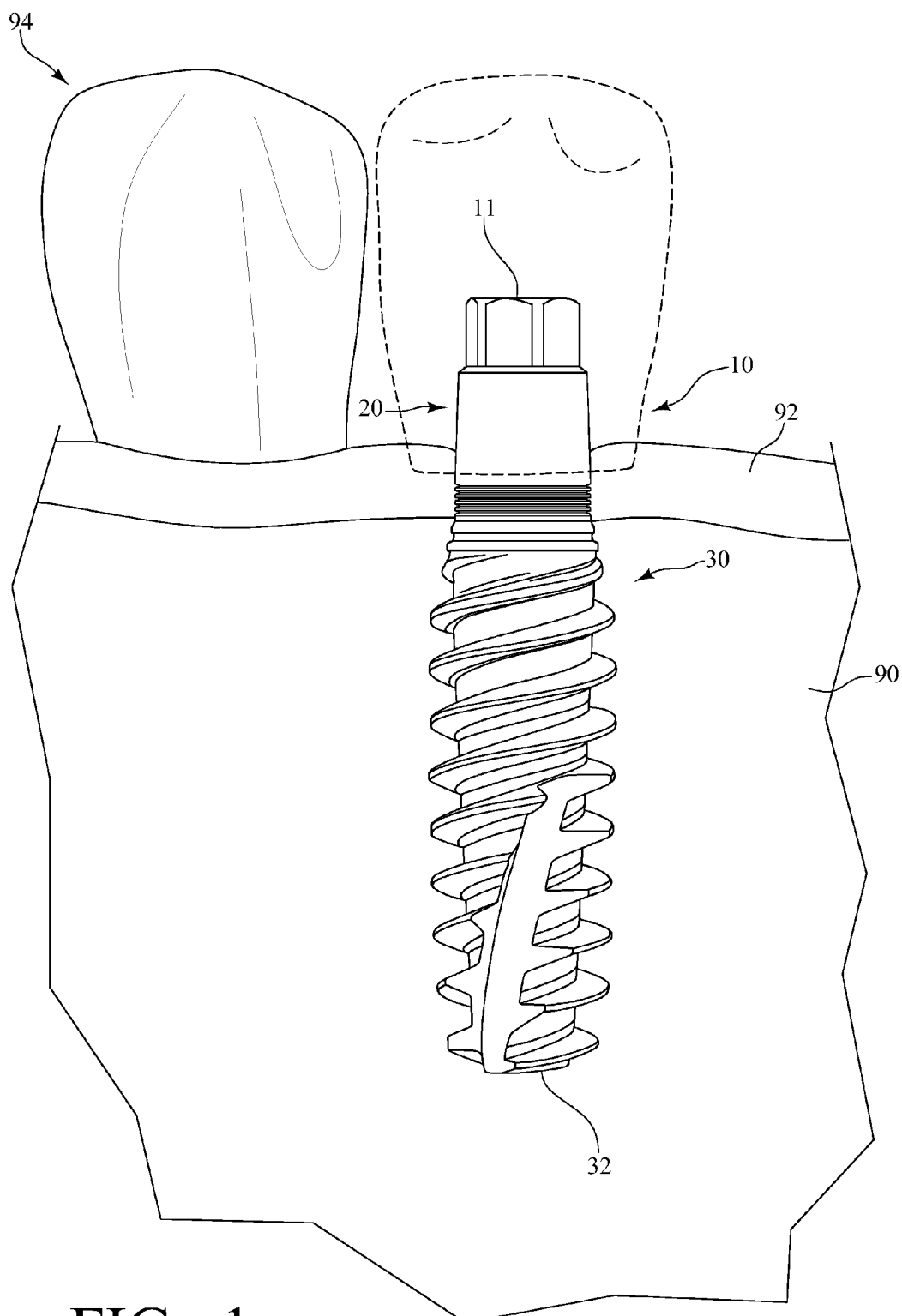
FIG. 1 is a perspective view of a dental device made in accordance with the present invention anchored in a lower jaw bone.

The dental devices depicted in the various Figures are selected solely for the purposes of illustrating the invention. Other and different dental devices may utilize the inventive features described herein as well. The illustrations are not intended to be representative with respect to dimensions.

Reference is first made to FIGS. 1 through 3A in which a dental device constructed in accordance with the present invention is generally noted by the character numeral 10. The dental device 10, which defines a distal abutment end 11 and a proximal end 32, has as major components an abutment section 20 and an implant section 30. The abutment section 20 comprises a first portion or stem 22, a second portion or collar 24, and a third portion or head 26. The abutment section 20 may be fixedly joined to the implant section 30, so the dental implant device is a one-piece unit; or, the abutment section 20 may be provided separate from the implant section 30 but adapted to be reversibly joined to the implant section 30.

Figure 2:
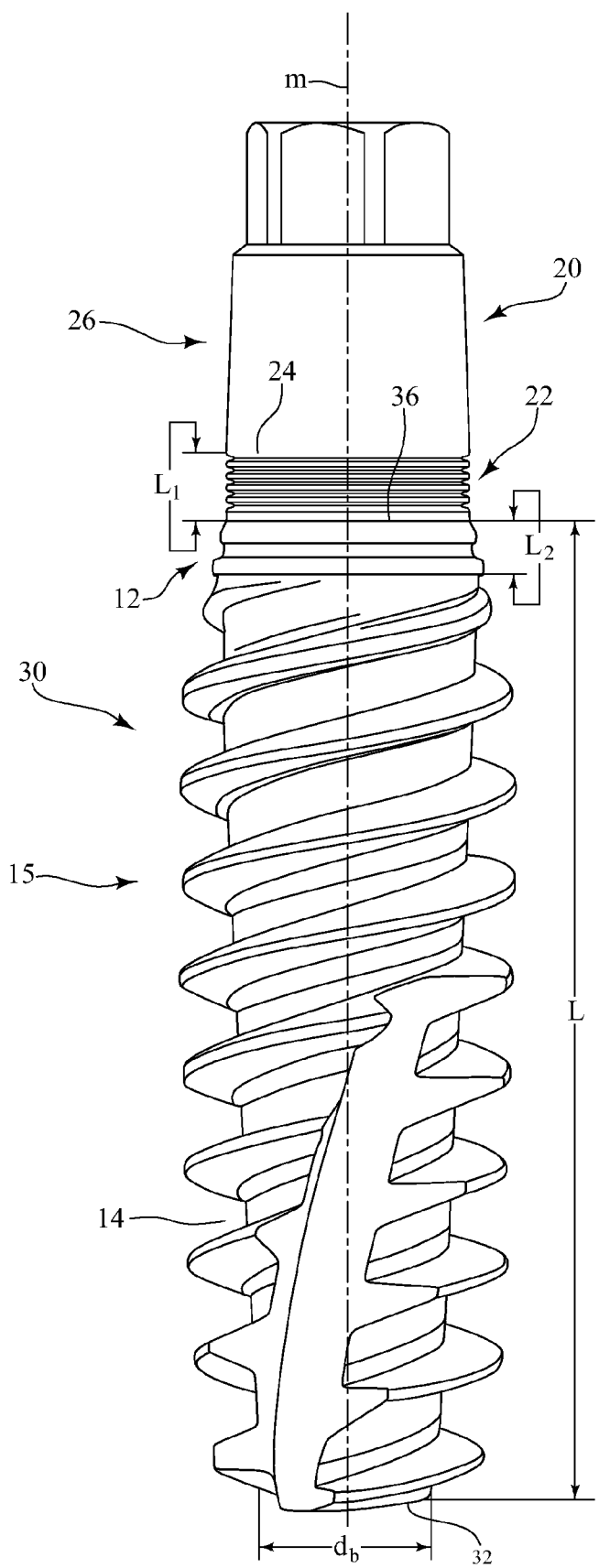
FIG. 2 is a side view of the dental device of FIG. 1.

The stem 22 of the abutment section 20 is adjacent to the implant section 30. The implant section 30 comprises a neck 12 and a body 15. In the embodiment of FIG. 2, the body 15 includes two different types of surface textures for inserting the implant 30 into the bone 90; however, the implant 30 may have any type of surface texture or configuration that is known in the art of dental implants to function as intended. As is known in the art, the implant section 30 includes a bore (not shown). The implant section 30 has an axial length, L, defined as the distance between an abutment end 36 and the proximal end 32. A midline, m, is defined through the axial center of dental device 10.

As shown in FIG. 1, the dental device 10 is mounted in a cavity bored into the jaw bone 90 of the patient such that the body 15 extends into the jaw bone 90. After the dental device 10 is anchored in the jaw bone 90, a bridge or artificial tooth 94 can be secured to the device 10, as is known in the art. The device 10 can be formed from any smooth hard material commonly known in the art as being suitable for dental implants, including but not limited to metals, ceramic-based materials, zirconium-based materials, and composites of these materials. In one embodiment, the device 10 is machined from a titanium alloy. The device 10 can be inserted into the cavity 92 by being screwed in or hammered in, techniques which are known in the art.

Figure 3:
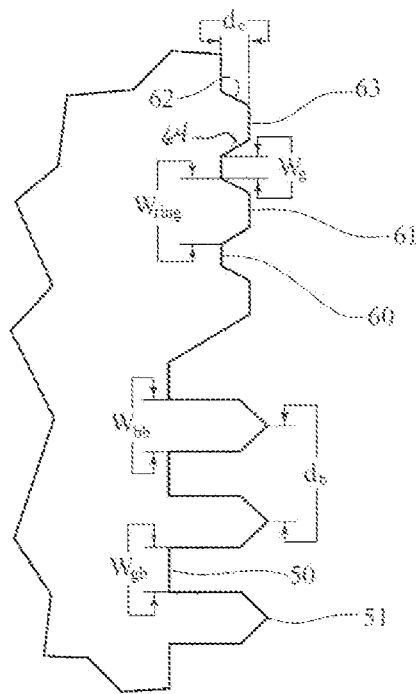
FIG. 3 is a detailed view of the connective tissue rings and grooves of the abutment section and of the bone locking rings and grooves of the implant section of the dental device of FIG. 2.
Figure 3A:
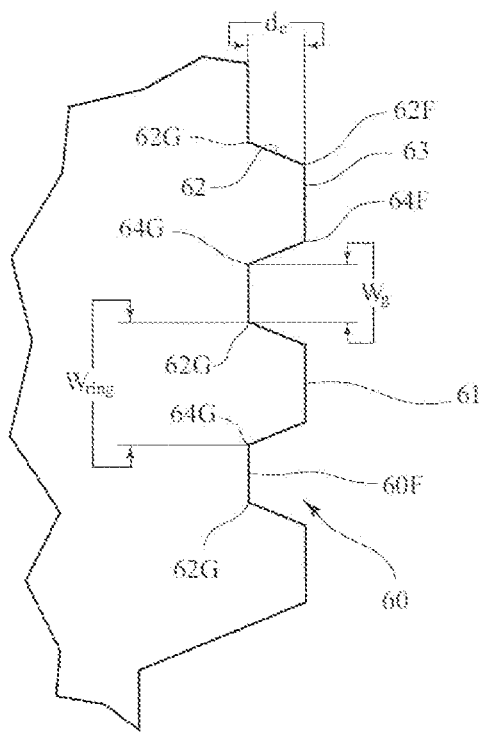
FIG. 3A is an expanded view of the connective tissue rings and grooves of the abutment section of the dental device of FIG. 2.

As shown in FIGS. 2, 3 and 3A, the abutment section 20 is adjacent to the implant section 30 such that the stem 22 abuts the neck 12. In an exemplary embodiment, the stem 22 defines a diameter at the stem's widest point wherein the stem diameter is smaller than either the diameter of the collar 24 or the diameter of the neck 12. When the dental device 10 is properly inserted into the jaw bone 90, the stem 22 will lie essentially at the upper edge of the bone and within a connective tissue layer 92.

Because of its proximity to the bone, it is imperative that the connective tissue forms a tight bond with the first portion of the abutment section 20. The present device 10, and particularly the stem 22, addresses this issue by utilizing a plurality of isolated grooves 60. Each groove 60 is formed between a pair of neighboring rings 61, wherein each ring 61 defines a closed loop—the beginning point joins the end point—which circumscribes the stem 22. By isolating each groove 60 two benefits are achieved over the prior art thread-like or spiral ring and groove designs: (1) soft tissue will grow into the isolated grooves 61 thereby providing a strong anchor for the implant and reducing the risk of implant loss; and, (2) any bacteria which may be present within a particular groove 60 is effectively contained within that groove reducing the probability of bacterial penetration along the implant and into the boney region causing infection at the implant site.

Referring again to FIGS. 2, 3 and 3A, the stem 22 has length $L_1$ of about 0.2 mm to about 2 mm, and comprises the band of rings 61 and grooves 60. As used herein, the band of rings 61 and grooves 60 comprise the connective tissue band. Each groove 60 is formed between a pair of neighboring rings 61. The connective tissue rings 61 and grooves 60 serve to help form a tight band of connective tissue around the stem 22. This can minimize the risk of bacterial invasion and can potentially limit bone loss. This may further mimic the Sharpey fiber attachment that is present on a natural tooth.

Each ring 61 of the stem 22 defines a closed loop—the beginning point joins the end point. Each ring 61 defines an outer diameter and each groove 60 defines an inner diameter. The difference between the outer diameter and the inner diameter defines a connective tissue groove depth, $d_c$. In the dental device 10, the groove depth $d_c$ is from greater than about 25 μm to about 600 μm, and more preferably from about 30 μm to about 400 μm. In an exemplary embodiment, the groove depth is about 50 μm.

Figure 4:
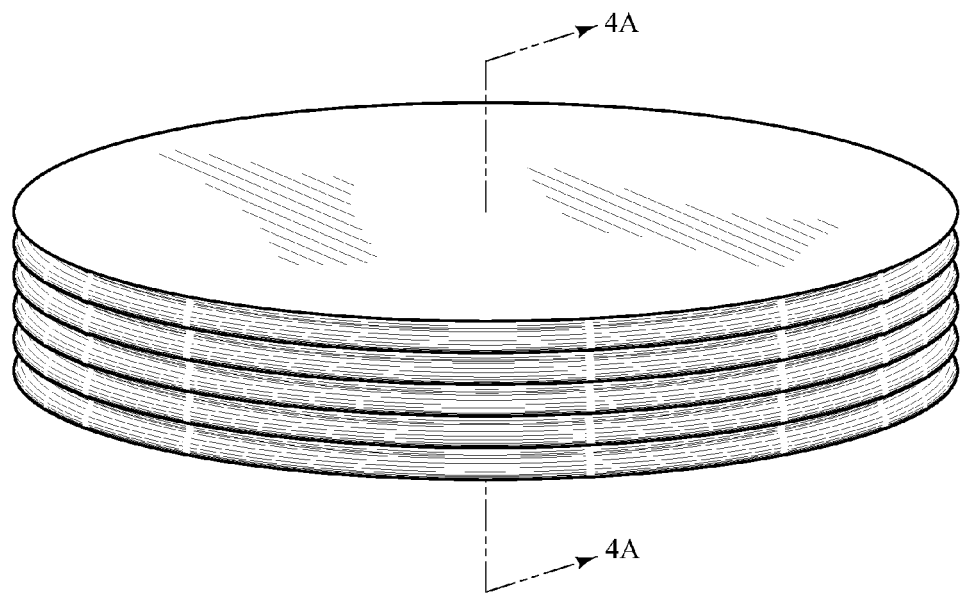
FIG. 4 is a first embodiment of the connective tissue grooves made in accordance with the present invention.
Figure 6:
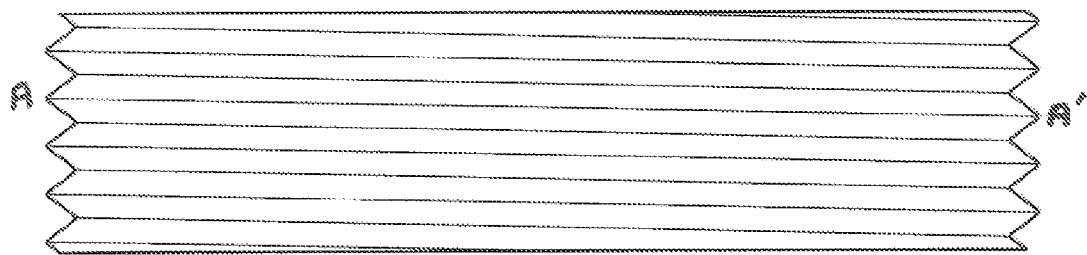
FIG. 6 is an alternative embodiment showing the connective tissues grooves at an angle.

Each ring 61 circumscribes the stem 22 one time forming a closed loop around the stem, such as would be obtained if a rubber band was wrapped around the stem 22. The rings 61 circumscribe the stem 22 so as to lie essentially parallel, and they are preferably essentially equally spaced relative to each other. The rings 61 may lie essentially perpendicular to the midline m, i.e. they can form a series of neighboring rings encircling the stem 22, as shown in FIG. 4, or they may lie at a slight angle relative to the midline m, thereby giving the stem 22 a spiraled appearance, as shown in FIG. 6, although each ring 61 would still form a closed loop (e.g, in FIG. 6, the ring formed by A-A' is a single loop running from A to A' and from A' to A in a reverse view (not shown)). Optionally, the rings 61 may be essentially planar or may have a slight "wave" so as to more closely match the bone contour. The rings 61 serve to isolate the grooves 60 so that bacteria and/or other contaminants cannot transverse the axial length of the dental device 10.

As shown in FIGS. 3 and 3A, each ring 61 has a face 63, an upper edge 62, and a lower edge 64. The angle of the edges 62, 64 relative to the face 63 may vary from a slight angle to essentially a right angle. The edge may be beveled or rounded slightly to eliminate sharp edges. The upper edge 62 has a groove end 62G and a face end 62F; the lower edge 64 has a groove end 64G and a face end 64F. The width of the ring 61, $w_{ring}$, is defined as the distance from the upper edge groove end 62G to the lower edge groove end 64G, and ranges from greater than about 25 μm to about 600 μm, and more preferably from about 30 μm to about 450 μm.

Each groove 60 defines a groove face 60F. A groove width, $w_g$, is defined to be equal to the length of the groove face 60F, and can range from greater than about 25 μm to about 600 μm, preferably from about 30 μm to about 150 μm, and more preferably from about 30 μm to about 135 μm.

In one embodiment, the ring width $w_{ring}$ and the groove width $w_g$ and the connective tissue groove depth $d_c$ are essentially identical. In a second embodiment, the ring edge 62 is approximately at a right angle to the face 63. In a preferred embodiment, the stem 22 has about fourteen grooves 60 covering a length of about 0.7 mm along the stem 22, and the ring width $w_{ring}$ and groove width $w_g$ and connective groove depth $d_d$ are each approximately 50 μm.

Referring again to FIGS. 2 and 3, the stem 22 lies adjacent to the neck 12 of the implant section 30. The neck 12 comprises a plurality of bone locking grooves 50. The neck 12 and bone locking grooves 50 may form only a relatively short portion along the implant section 30, as shown in FIG. 2, with macro grooves 14 or other surface textures as are known in the art covering the body 15. Alternatively, the neck 12 and bone locking grooves 50 may extend from the stem 22 to the proximal end 32 of implant section 30. In a preferred embodiment, the neck 12 has an axial length, $L_2$, of from about 0.1 mm to about 16 mm.

Figure 7:
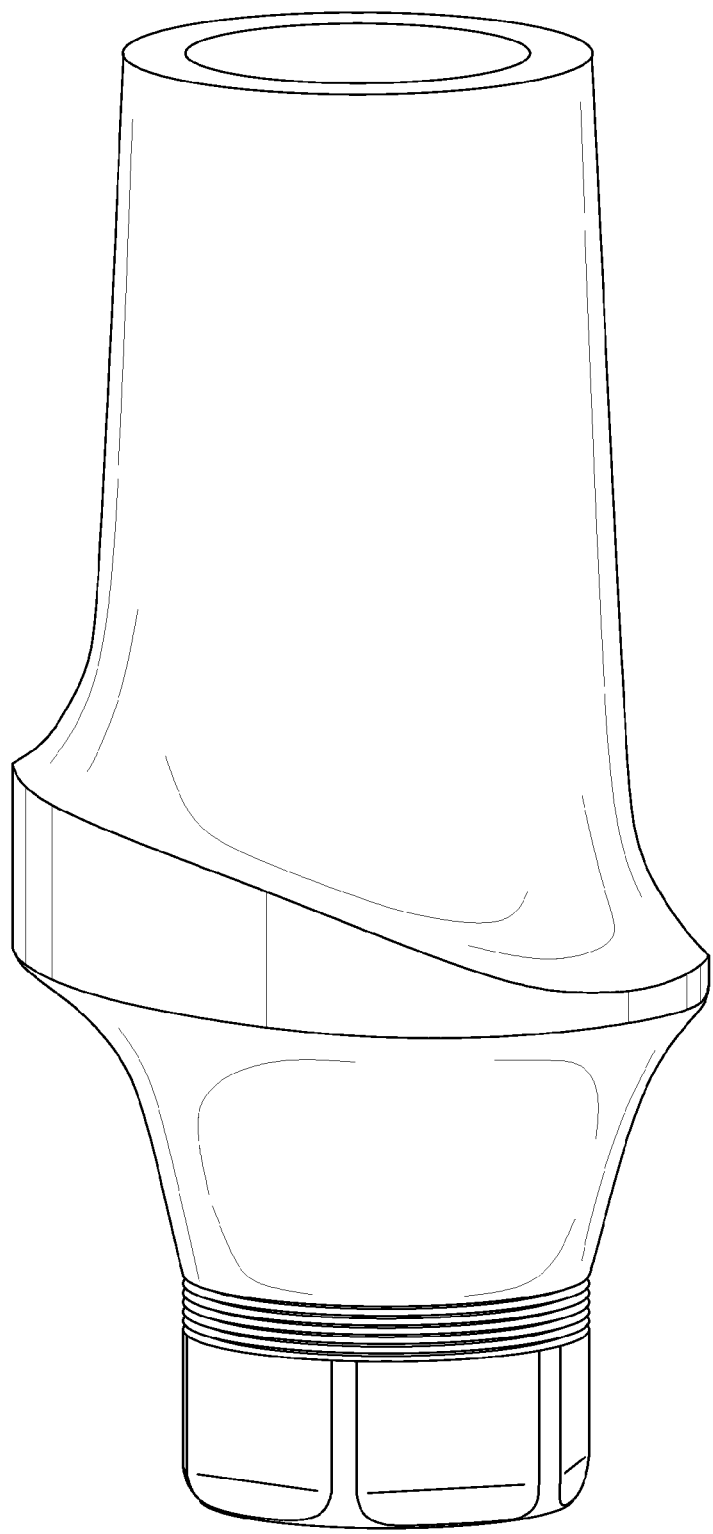
FIG. 7 is perspective view of an abutment having connective tissues grooves made in accordance with the present invention.

In the embodiment shown in FIG. 2, the dental device 10 has an essentially cylindrical shape. However, other configurations known in the art, such as implants with a frusto-conical shape, can apply the band and groove technology described herein. As shown in FIG. 2, the dental device 10 is a one-piece unit comprising an abutment section 20 and an implant section 30. Optionally, the dental device 10 may be divided into separate pieces that can be reassembled to create the device 10. For example, it is anticipated that the device 10 could be divided into an abutment section 120 having connective tissue grooves, as shown in FIG. 7, and having a separate implant section (not shown), the division being made along the abutment end 36. The stem 22, neck 12 and other exterior faces of the dental device 10 may have a smooth, porous, coated, treated, textured, roughened, machined or beaded surface comprised of a network of discrete particles which provides interstices into which bone is permitted to grow once implant 10 is accommodated within the bone 90 (such as described in U.S. Pat. No. 6,379,153, issued to Schroering, and incorporated herein in its entirety by reference, or roughened by other techniques known in the art).

Several optional features, known in the art and not shown herein, may be included in the implant 10. For example, the implant 10 may be self-tapping to allow the implant 10 to enter the jaw bone more easily and/or may include a cutting thread. Cutting threads are commonly used to help seat the dental implants.

The ring and groove designs disclosed herein are anticipated to be applicable to implant designs other than the implant depicted in FIG. 2. For example, in the implant described in U.S. Pat. No. 6,379,153 issued to the applicant, the smooth-surfaced neck (44) can be replaced by the bone locking grooved neck 12 taught herein and the abutment section 20, comprising the stem 22 with the connective tissue rings 61 and grooves 60, can be adjoined to the implant (10). The resulting dental device would provide for a tapered body with a beaded finish between the bone locking grooves 16 and the proximal end 32.

Figure 4A:
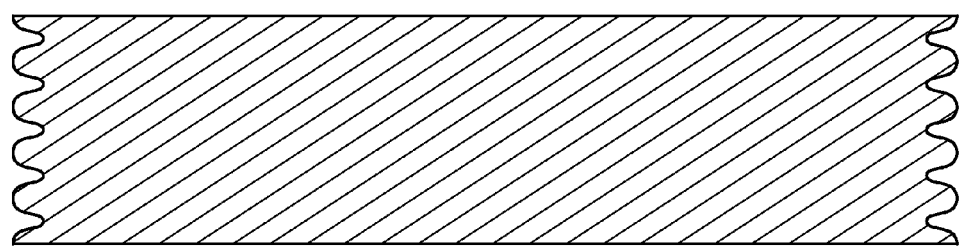
FIG. 4A is a cross-sectional view taken along line 4A-4A of the connective tissue grooves of FIG. 4.
Figure 5A:
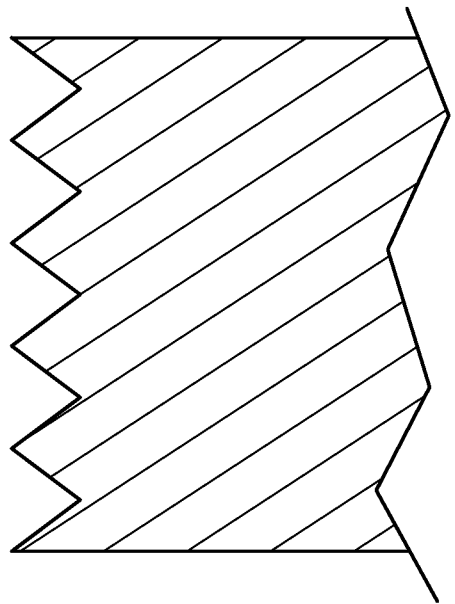
FIGS. 5A-5H are alternative embodiments of connective tissue grooves made in accordance with the present invention.
Figure 5B:
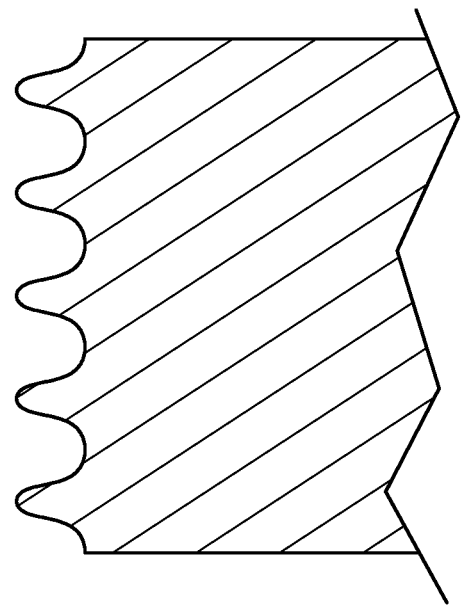
Figure 5C:
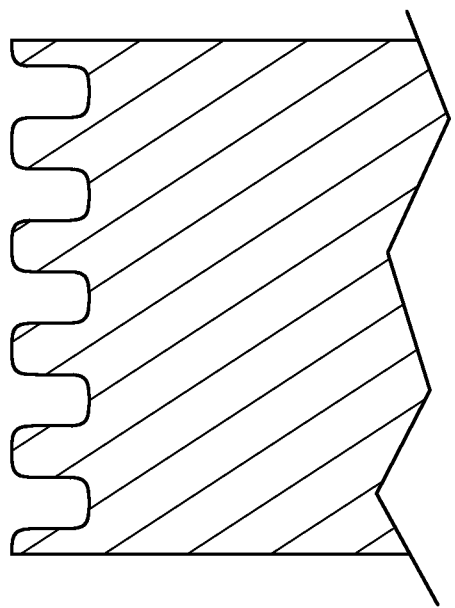
Figure 5D:
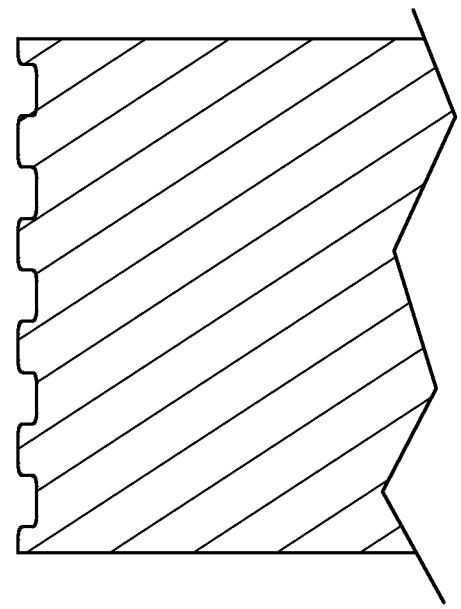
Figure 5E:
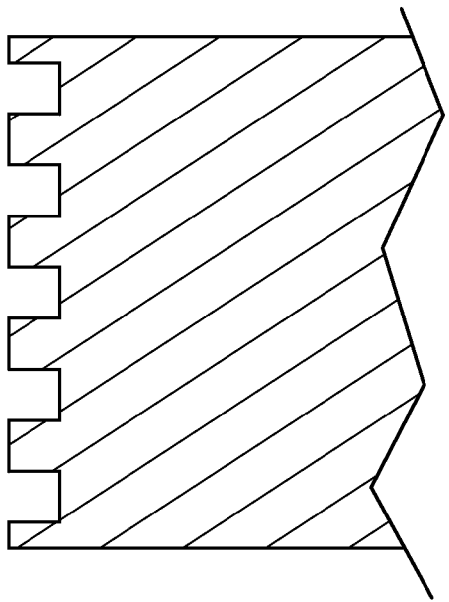
Figure 5F:
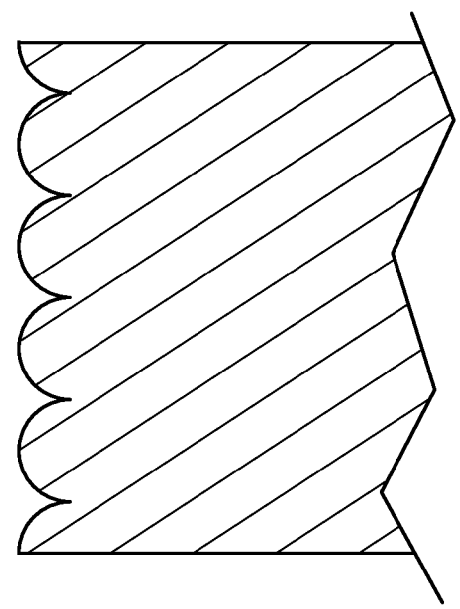
Figure 5G:
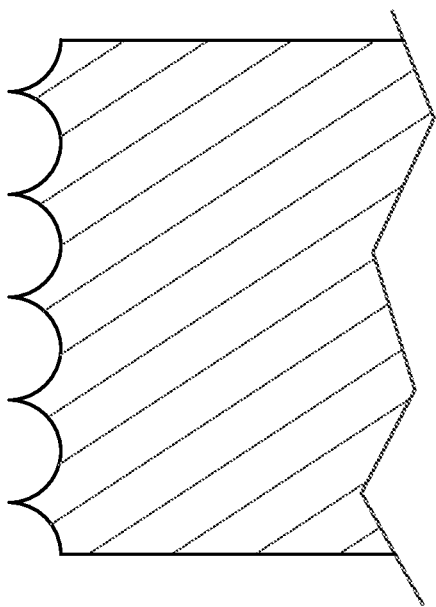
Figure 5H:
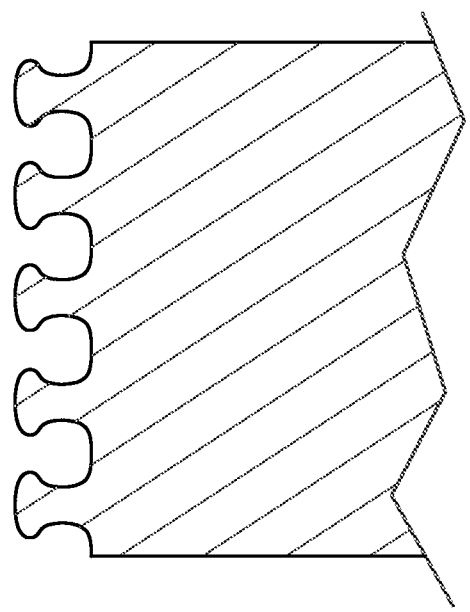

Further, it is anticipated that the band of rings 61 that form the connective tissue band may vary in design and/or that the surface may be roughened. For example, as shown in FIGS. 4 and 4A, the rings 61 may be in the form of parallel rings with slightly rounded edges. Alternatively, the rings may have a variety of edge designs, such as shown in FIGS. 5A-5G.

It is understood that, in light of a reading of the foregoing description and drawings, those with ordinary skill in the art will be able to make changes and modifications to the present invention without departing from the spirit or scope of the invention, as defined herein. For example, those skilled in the art may accomplish the band and groove patterns by using bands with tips of a different design or configuration.

What is claimed is:

1. A dental implant system comprising a dental implant device for anchoring in bone, said dental implant device defining a stem having a connective tissue band circumscribing said stem wherein said connective tissue band comprises:
   (a) a plurality of neighboring individual rings, wherein each individual ring is defined as a closed loop having no distinguishable beginning or end and wherein each individual ring defines an outer diameter; and
   (b) a plurality of grooves, wherein each groove is formed between two of said neighboring individual rings and wherein each groove defines an inner diameter,
   and wherein the connective tissue band defines a connective tissue groove depth equal to the difference between the outer diameter and the inner diameter, and wherein said connective tissue groove depth measures from greater than 25 μm to 400 μm, wherein said rings are contoured to match a jaw bone and said rings define a ring width and said ring width ranges from greater than 25 μM to 600 μm.

2. The dental implant system of claim 1 wherein said stem has a length of 0.2 mm to 2 mm.

3. The dental implant system of claim 1 wherein said connective tissue groove depth measures 50 μm.

4. The dental implant system of claim 1 wherein said rings lie essentially parallel and are essentially equally spaced relative to each other.

5. The dental implant system of claim 4 wherein said rings lie at a slight angle relative to a midline of said dental implant device.

6. The dental implant system of claim 1 wherein said grooves define a groove width and said groove width ranges from greater than 25 μm to 600 μm.

7. The dental implant system of claim 6 wherein said groove width ranges from 30 μm to 450 μm.

8. The dental implant system of claim 1 wherein an abutment is removably joined to said dental implant device.

9. The dental implant system of claim 1 wherein an abutment is fixedly joined to said dental implant device.

\* \* \* \* \*